(12) United States Patent
Maspoch Comamala et al.

(10) Patent No.: US 9,352,489 B2
(45) Date of Patent: May 31, 2016

(54) METHOD FOR THE PREPARATION OF METAL ORGANIC FRAMEWORKS

(71) Applicant: FUNDACIÓ INSTITUT CATALÀ DE NANOCIÈNCIA I NANOTECNOLOGIA, Bellaterra (ES)

(72) Inventors: Daniel Maspoch Comamala, Sant Cugat del Vallès (ES); Inhar Imaz, Barcelona (ES); Arnau Carné Sánchez, Manresa (ES); Antonia Maria Cano Sarabia, Alguazas (ES)

(73) Assignee: FUNDACIÓ INSTITUT CATALÁ DE NANOCIÈNCIA I NANOTECNOLOGIA, Bellaterra (ES)

( * ) Notice: Subject to any disclaimer, the term of this patent is extended or adjusted under 35 U.S.C. 154(b) by 242 days.

(21) Appl. No.: 14/350,024

(22) PCT Filed: Oct. 3, 2012

(86) PCT No.: PCT/EP2012/069511
§ 371 (c)(1),
(2) Date: Apr. 4, 2014

(87) PCT Pub. No.: WO2013/050402
PCT Pub. Date: Apr. 11, 2013

(65) Prior Publication Data
US 2014/0284829 A1 Sep. 25, 2014

(30) Foreign Application Priority Data
Oct. 4, 2011 (EP) ..................................... 11183773

(51) Int. Cl.
| | | |
|---|---|---|
| B01J 20/22 | (2006.01) | |
| C07F 19/00 | (2006.01) | |
| B29B 9/12 | (2006.01) | |
| B01J 31/16 | (2006.01) | |
| C07F 15/02 | (2006.01) | |
| C07F 1/00 | (2006.01) | |
| C07F 3/00 | (2006.01) | |
| C07C 51/41 | (2006.01) | |

(52) U.S. Cl.
CPC ................ *B29B 9/12* (2013.01); *B01J 20/226* (2013.01); *B01J 31/16* (2013.01); *B01J 31/1691* (2013.01); *C07C 51/412* (2013.01); *C07C 51/418* (2013.01); *C07F 1/005* (2013.01); *C07F 3/003* (2013.01); *C07F 15/025* (2013.01); *C07F 19/00* (2013.01)

(58) Field of Classification Search
None
See application file for complete search history.

(56) References Cited

U.S. PATENT DOCUMENTS

| | | | |
|---|---|---|---|
| 2004/0097724 A1 | 5/2004 | Muller et al. | |
| 2007/0227898 A1* | 10/2007 | Muller | B01J 20/226 205/457 |
| 2009/0042000 A1 | 2/2009 | Schubert et al. | |
| 2010/0076220 A1 | 3/2010 | Schubert et al. | |
| 2010/0197990 A1* | 8/2010 | Schubert | B01J 20/22 585/830 |
| 2012/0055880 A1 | 3/2012 | Loiseau et al. | |
| 2013/0012717 A1* | 1/2013 | Trukhan | C07F 3/06 548/101 |

FOREIGN PATENT DOCUMENTS

| | | |
|---|---|---|
| EP | 1070538 B1 | 9/2004 |
| EP | 1373277 B1 | 12/2008 |
| WO | WO02070526 A1 | 9/2002 |
| WO | WO2010058123 A1 | 5/2010 |

OTHER PUBLICATIONS

Chalati T., Horcajada P., Gref R., Couvreur P., Serre C. "Optimization of the synthesis of MOF nanoparticles made of flexible porous iron fumarate MIL-88A", Journal of Materials Chemistry, Feb. 21, 2011, Issue 7, vol. 21, p. 2220-2227, Royal Society of Chemistry, London UK.

Chen B., Ockwig N. W., Millward A. R., Contreras D. S., Yaghi O.M. "High H2 adsorption in a microporous metal-organic framework with open metal sites", Angewandte Chemie International Edition, Jul. 25, 2005, vol. 44, Issue 30p. 4745-4749, Wiley-VCH Verlag GmbH & Co. KGaA, Weinheim, Germany.

Chui S. S. Y., Samuel L. M. F., Chamant J. P. M., Orpen A. J, Williams I. D. "A chemically functionalizable nanoporous material [Cu3(TMA)2(H2O)3]n", Science, Feb. 19, 1999, vol. 283, No. 5405, pp. 1148-1150m, American Association for the Advancement of Science, Washington DC.

(Continued)

Primary Examiner — Mary F Theisen
(74) Attorney, Agent, or Firm — Peter B. Scull; Hamilton, DeSanctis & Cha LLP (57) ABSTRACT

A process for the preparation of a dry crystalline metal organic framework which comprises: a) spray drying at least one metal ion and at least one organic ligand which is at least bidentate into a spray dryer in the presence of a solvent, wherein the reaction of the at least one metal ion with the at least one organic ligand to yield the metal organic framework and the drying of the obtained metal organic framework take place simultaneously inside the spray dryer, and b) collecting the formed dry crystalline metal organic framework.

14 Claims, 5 Drawing Sheets

(56) References Cited

OTHER PUBLICATIONS

Rosi N. L., Kim J., Eddaoudi M., Chen B., O'Keeffe M., Yaghi O. M. "Rod packings and metal-organic frameworks constructed from rod-shaped secondary building units", Journal of the American Chemical Society, Jan. 13, 2005, vol. 127(5), p. 1504-1518, American Chemical Society, Washington DC.

International Search Report and Written Opinion for PCT application No. PCT/EP2012/069511, International Filing Date: Oct. 3, 2012, Mail date: Dec. 18, 2012) performed by the European Patent Office, Rijswijk NL.

* cited by examiner

METHOD FOR THE PREPARATION OF METAL ORGANIC FRAMEWORKS

The present invention is related to the field of material chemistry, particularly, metal organic chemistry. The invention provides a method for the industrial preparation of metal organic frameworks.

BACKGROUND ART

Metal organic frameworks, also termed MOFs, form an interesting class of microporous or mesoporous substances having characteristics which allow their use in many technical fields, such as storage, separation or controlled release of chemical substances, catalysis and drug delivery. These potential applications are a direct consequence of the porous architecture of MOFs, which leads to high specific surface area of these materials.

MOFs are composed of two major components: a metal ion or cluster of metal ions and an organic molecule that plays the role of a ligand. The organic units are typically di-, tri- or polydentate ligands. The choice of metal and organic ligand has significant effects on the structure and properties of the MOF. For example, the metal coordination preference influences the size and shape of pores by dictating how many ligands can bind to the metal and in which orientation.

MOFs are produced almost exclusively by hydrothermal or solvothermal techniques, where crystals are slowly grown from a hot solution of metal precursor, such as metal salts, and bridging ligands. Since ligands in MOFs typically bind reversibly, the usual slow growth of crystals allows defects to be redissolved, resulting in a material with milli- and micrometer-scale crystals and a near-equilibrium defect density.

As a result of their industrial applicability, preparation of porous MOFs has attracted a interest over the last years, with numerous strategies having been described in the literature. For instance, WO2010058123 and EP1070 538 disclose methods for hydrothermal preparation of MOFs. Similarly, US20100076220 discloses a process for the obtaining of crystalline porous metal organic compounds in a liquid phase at elevated temperature.

However, the use of MOFs for industrial applications, such as storage materials for consumer products, demands an immense scale-up of their synthesis. Most of the available methodologies imply the use of high temperatures, high pressure and long crystallization times. The required conditions thus obstruct considerably the scale-up of MOF preparation which is required for industrial application.

A scaled-up process using mild conditions has been disclosed in US20090042000. This patent application discloses the preparation of kilogram quantities of Cu-benzene-1,3,5-tricarboxylic acid (1,3,5-BTC) by reacting an admixture of a copper nitrate with 1,3,5-BTC in the liquid phase at atmospheric pressure above 80° C. Still, long crystallization times between 15 and 96 hours are needed to obtain the crystalline MOF.

Shorter reaction times with mild conditions are disclosed in EP1373277. This document describes a method for the hydrothermal preparation of zinc terephthalate framework with good yields, the method comprising the reaction of an admixture of a zinc salt with terephthalic acid. The method requires the presence of a base (thriethylamine) and a lactam or a lactone solvent. However, even though the reaction time is shortened with respect to other methods, at least 3 hours of continuous stirring are needed to obtain a small quantity of MOF product, and no scale up has been attempted.

Additionally, all known preparation processes require the obtained MOF crystal to be separated from the mother liquor and further dried to obtain the final MOF product. The separation and drying steps add up to the already long preparation times.

Thus, even though a considerable improvement has been made in the art in the preparation of MOFs by hydrothermal methodologies, MOF preparation methods known in the art are not efficient for large-scale industrial preparation.

SUMMARY OF THE INVENTION

The inventors have developed a new method for the preparation of MOFs that is particularly appropriate for industrial large-scale production.

The inventors have surprisingly found that by spray drying a metal ion and an organic ligand which is at least bidentate into a spray dryer in the presence of a solvent it is possible to synthesize MOFs, directly obtaining dry MOF crystals with good yield, by a process which uses mild conditions, regular industrial equipment and where the reaction time is drastically reduced.

Thus, in a first aspect, the invention provides a process for the preparation of a dry crystalline MOF which comprises: a) spray drying at least one metal ion and at least one organic ligand which is at least bidentate into a spray dryer in the presence of a solvent, wherein the reaction of the at least one metal ion with the at least one organic ligand to yield the MOF and the drying of the obtained MOF take place simultaneously inside the spray dryer, and b) collecting the formed dry crystalline MOF.

"Metal Organic Frameworks", also termed MOFs, are crystalline compounds consisting of metal ions coordinated to often rigid organic molecules to form one-, two-, or three-dimensional structures that are highly porous.

By "organic ligand which is at least bidentate" it is understood an organic compound that is able to bind at least two metal ions through coordination bonds.

The term "spraying" (also known as atomizing) refers to the process of forming a spray, which is a dynamic collection of drops dispersed in a gas.

A "spray dryer" is a device well known in the state of the art where a liquid input stream is sprayed in small droplets through a nozzle (or atomizer) into a hot gas stream.

As compared to other MOF production processes, the process of the invention greatly reduces the reaction time needed for the synthesis of MOFs. The process also has the advantage that it directly produces dry crystalline MOFs out of the initial liquid reagents, thus avoiding a filtering step and further contributing to the efficiency of MOF preparation.

Importantly, because it employs mild conditions and can be performed in regular industrial spray dryer devices, another advantage of the present process is that it is easily scaled-up to produce large quantities of dry MOF crystals in a very short time. Further, the process can be applied to a continuous or semi-continuous flow production process. The reagents can be continuously sprayed at the top of the spray drying apparatus while the newly formed crystals fall to the bottom and can be collected in the drum. Typically, the raw product is obtained as a dry powder containing small MOF crystals, although it may also be obtained as agglomerate. As crystals are formed inside the spray dryer and fall to the bottom, new reactants are sprayed and the product is continuously produced. The only limitation of the process is the capacity of the drum, and even then, the process needs to be stopped only time enough for the drum to be emptied. Furthermore, this limitation can be eradicated by installing a continuous unloading system for the drum.

In principle, any MOF can be prepared following the present process with relatively high purity and good yield. The examples below show the production of several MOFs. The crystals directly obtained by the process of the invention may have a purity up to 99% (w/w). Additional washing and drying steps result in substantially pure crystals. Further, MOF crystals obtained by the present process have particularly small dimensions. The small size of the crystals is an advantage for certain applications. For instance, small crystals are beneficial for biomedical applications, such as drug delivery and also for using MOFs as contrast agents. Additionally, the small size of the MOF crystals obtainable by the process of the invention can provide special properties for gas sorption applications.

MOFs are particular materials in that they are highly porous, and it is precisely this property that renders them ideal for gas storage, controlled release, catalysis and most of their industrial applications. It is therefore important that the obtained MOFs have a high specific surface area. As shown in the examples below, specific surface area as measured by the Brunauer-Emmett-Teller (also known as BET) method for the MOFs obtained by the process of the invention is very high. Altogether, the present process results in high-quality MOFs.

The process of the invention thus provides for the short-time, large-scale production of MOFs with yields comparable to previously known processes which are either non-scalable or time consuming. Altogether, the present invention provides an efficient and economical process for use in industrial MOF preparation.

Surprisingly, the process disclosed herein can yield MOF crystals in the form of spherical microcapsules. This microcapsule form can be maintained after washing of the MOF product with organic solvents, as to obtain a final spherical microcapsule crystalline product. Direct obtaining of microcapsules is advantageous for certain applications, for example, active ingredient encapsulation and controlled release, or for the preparation of selective microreactors containing molecular catalysts. The obtained microcapsules demonstrate a selective permeability directly related to the micropore size of the MOF crystals forming the capsule wall.

DETAILED DESCRIPTION OF THE INVENTION

The present invention provides a process for the large-scale, continuous-flow production of MOFs suitable for industrial applications. Such process comprises spray drying at least one metal ion and at least one organic ligand which is at least bidentate in the presence of a solvent, and collecting the formed MOF crystals.

The metal ions for use in the process of the invention are those usually employed for the preparation of MOFs. Non-limiting metal ions are those from chemical elements in the following groups: alkali metals (Li, Na, K, Rb, Cs, Fr), alkaline earth metals (Be, Mg, Ca, Sr, Ba, Ra), transition metals (Sc, Y, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg) and post-transition metals (Al, Ga, In, Tl, Sn, Pb, Bi), as well as metalloids (B, Si, Ge, As, Sb, Te, Po), lanthanides (La, Ce, Pr, Nd, Pm, Sm, Eu, Gd, Tb, Dy, Ho, Er, Tm, Yb, Lu) and actinides (Ac, Th, Pa, U, Np, Pu, Am, Cm, Bk, Cf, Es, Fm, Md, No, Lr). Unusual metals not mentioned above or newly discovered could be also used in the method of the invention. In one embodiment the at least one metal ion is selected from the group consisting of Zn, Cu, Ni, Co, Fe, Mn, Cr, Cd, Mg, Ca, Zr, Gd, Eu, Tb, and mixtures thereof. In a preferred embodiment the at least one metal ion is selected from the group consisting of Zn, Cu, Fe, Gd, Mg, and mixtures thereof.

Usually, the metal ion is provided in the form of a salt. Non-limiting examples of metal salts for use in the invention are nitrates, chlorides, sulphates, acetates, acetylacetonates, bromides, carbonates, tartrates and perchlorates.

In certain embodiments, MOF formation can take place by reacting more than one metal ion. In one embodiment the process of the invention is performed by reacting between one and six different metal ions. In a preferred embodiment the process of the invention is performed by reacting between one and three different metal ions. In a more preferred embodiment the process of the invention is performed by reacting between one and two different metal ions. For example, the MOF can be synthesized by reacting two metal ions with at least one organic ligand which is at least bidentate according to the present invention.

According to the invention it is also possible that the MOF is formed by the reaction of one or more metal ions with one or more organic ligands. In one embodiment the process of the invention is performed by reacting between one and six organic ligands which are at least bidentate. In a preferred embodiment the process of the invention is performed by reacting from one to three organic ligands which are at least bidentate. In a more preferred embodiment the process of the invention is performed by reacting from one to two organic ligands which are at least bidentate.

Thus, the metal ion or ions coordinate with one or more organic compounds that act like a ligand. The organic ligands in the sense of the present invention must be at least bidentate, meaning that they must be able to bind at least two metal ions by coordination bonds. The organic ligands according to the invention can be bidentate, but also tridentate, tetradentate or pluridentate in the sense that they may coordinate two, three, four or multiple metal ions through coordination bonds. In one embodiment, the organic ligand coordinates between 2 and 20 metal ions. In a preferred embodiment, the organic ligand coordinates between 2 and 12 metal ions. In a more preferred embodiment, the organic ligand coordinates between 2 and 8 metal ions. The ability to coordinate metal ions is conferred by certain functional groups. Non-limiting functional groups that can be contained by the organic ligand to form a MOF according to the invention are —COOH, —CSSH, —NO$_2$, —B(OH)$_2$, —SO$_3$H, —Ge(OH)$_3$, —Sn(OH)$_3$, —Si(SH)$_4$, —Ge(SH)$_4$, —Sn(SH)$_3$, —PO$_3$H, —AsO$_3$H, —AsO$_4$H, —P(SH)$_3$, As(SH)$_3$, C$_4$H$_2$O$_4$, —RSH, —RNH$_2$, —RNR—, —ROH, —RCN, —PO(OR)$_2$, —RN$_3$, where R is hydrogen, alkyl, alkylene, preferably C1, C2, C3, C4 or C5 alkylene, or aryl group, preferably comprising 1 or 2 aromatic nuclei.

In one embodiment, the at least one organic ligand which is at least bidentate contains functional groups selected from the group consisting of a carboxylate, a phosphonate, an amine, an azide, a cyanide, a squaryl, an heteroatom, and mixtures thereof. Preferred heterocycles contain O, S and/or N. Non-limiting examples of preferred heterocycles in the sense of the invention are azoles, pyridines and diazines.

The at least one organic ligand which is at least bidentate may be comprised of at least one functional group as mentioned above bound to any suitable organic compound, provided that it is ensured that the organic ligand is capable of coordinating at least two metal ions.

In another embodiment, the at least one organic ligand which is at least bidentate is a monocarboxylic acid, a dicarboxylic acid, a tricarboxylic acid, a tetracarboxylic acid, imidazole, or mixtures thereof.

In a preferred embodiment, the at least one organic ligand which is at least bidentate is selected from the group consisting of formic acid, acetic acid, oxalic acid, propanoic acid, butanedioic acid, (E)-butenedioic acid, benzene-1,4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E,4E)-hexa-2,4-dienedioic acid, 1,4-naphthalenedicarboxylic acid, naphthalene-2,6-dicarboxylate, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, 1,4-diazabicyclo[2.2.2]octane, pyridine-4-carboxylic acid, pyridine-3-carboxylic acid, imidazole, 1H-benzimidazole, 2-methyl-1H-imidazole, and 4-methyl-5-imidazolecarboxaldehyde.

In another embodiment, the at least one organic ligand which is at least bidentate is a peptide.

The process of the invention requires that a solvent is present for the reagents to form the MOF. The term "solvent" relates to individual solvents and also to mixtures of different solvents. The solvent can be any aqueous or non-aqueous solvent. In certain embodiments of the invention, mixtures of two or more solvents are used. In a preferred embodiment, the solvent is selected from the group consisting of water, (C1-C6)-alcohols, (C5-C7)-alkanes, alkenes, (C3-C8)-cycloalkanes, N,N-dimethyl formamide (DMF), N,N-diethyl formamide (DEF), dimethyl sulfoxide (DMSO), dioxane, chloroform, dichloromethane, diethyl ether, acetonitrile, toluene, benzene, tetrahydrofuran (THF), chlorobenzene, ethylene glycol, and mixtures thereof. Preferred alcohols are methanol, ethanol and isopropanol. Preferred alkanes are hexane, heptane and pentane.

There are several ways in which the reagents can be fed to the spray dryer with no apparent change in the obtained MOF. For instance, a solution comprising both the at least one metal ion and the at least one organic ligand which is at least bidentate can be sprayed into the spray dryer apparatus in the presence of a solvent. The moment this solution is sprayed into the spray dryer the reaction and the drying takes place and dry MOF crystals are formed. Thus, in one embodiment, the process of the invention comprises spraying a liquid solution containing both the at least one metal ion and the at least one organic ligand which is at least bidentate into a spray dryer in the presence of a solvent. The solvent is usually included in the sprayed solution comprising the at least one metal ion and the at least one organic ligand. Additionally, more solvent can be simultaneously sprayed through a different nozzle.

Alternatively, two different solutions, one containing the at least one metal ion and the other one containing the at least one organic ligand, can be simultaneously fed to the spray dryer through separate nozzles or a three-fluid nozzle. Thus, in one embodiment, the process of the invention comprises simultaneously spraying two liquid solutions, one containing the at least one metal ion and another containing the at least one organic ligand, into a spray dryer in the presence of a solvent. The solvent can be fed to the reaction contained in either the metal ion or the organic ligand solution, or it may be contained in both solutions. Additionally, more solvent can be simultaneously sprayed through a different nozzle or a multi-fluid nozzle.

In a particular embodiment, the process of the invention also comprises the addition of a base. The synthesis of MOFs may benefit from the presence of a base in the reaction mixture, since the base can further reduce the reaction time and/or the reaction temperature. The base can be sprayed into the spray dryer together with one of the reactants, together with the solvent, it can be simultaneously sprayed through a different nozzle, or a combination thereof. Preferably, the base is not contained in the liquid solution containing both the metal ion and the at least bidentate organic ligand. In principle any base can be used in the method of the invention. However, preferred bases are selected from the group consisting of metal alkaline or earth alkaline hydroxides, amines, metal alkaline or earth alkaline carbonates, metal alkaline or earth alkaline acetates, pyridines, azoles, diazines, and mixtures thereof.

Any regular spray dryer can be employed to produce dry crystalline MOFs according to the invention. Preferably, large industrial spray dryers are used. Such industrial spray dryers can produce very large quantities of MOFs according to the present method in surprisingly short times. The spray dryer must have as many holes as are required for the spraying of the reactants, solvents and, optionally, the base. Usually, air is employed as the hot gas stream, however, other gases can be employed, such as nitrogen. Industrial spray dryers have large capacity drums for product collection. Preferably, the spray dryer drum is coupled to a powder-removing device. The device removes the formed MOF powder at regular intervals, making place for newly synthesized MOF, such that the production must not be regularly stopped to empty the drum. Thus, in a particular embodiment, the process for the preparation of a dry crystalline MOF according to the invention is a continuous process.

As mentioned above, the preparation of MOFs according to the present process can proceed at mild conditions, such that it is particularly appropriate for large-scale industrial production. The reaction temperature inside the spray dryer can be comprised between 20 and 350° C. but, preferably, the temperature is between 50 and 250° C., more preferably between 60 and 200° C., more preferably between 80 and 200° C., more preferably between 100 and 180° C., and still more preferably between 120 and 180° C.

As mentioned above, the reaction time required for the preparation of MOFs according to the present process is surprisingly short. Usually, the reaction time is below 6 hours to obtain the dry product. Preferably, the reaction time is between 3 minutes and 4 hours, more preferably between 5 minutes and 4 hours, more preferably between 7 minutes and 3 hours, more preferably between 8 minutes and 2 hours, more preferably between 9 minutes and 1 hour, and still more preferably between 10 minutes and 30 minutes.

The person skilled in the art is aware that the reaction parameters need to be optimised for each MOF product and each spray-dryer. For instance, reagent concentrations, choice of solvent, choice of base, gas spray flow, drying gas flow, feed flow and temperature, among others, are parameters to be adjusted. Particularly, the spray-dryer being employed can highly influence process parameters. The skilled person knows how to adjust the parameters in order to obtain the required product.

The MOF crystals obtained by the process of the present invention have a high purity grade. Nevertheless it is typical for MOF products to be subjected to a purification step. Thus, in one embodiment, the process of the invention additionally comprises a purification step. Usually, this purification step comprises washing the MOF crystals with an appropriate solvent and drying. This purification step is also known as "extraction step" because it removes the solvent or other molecules that are retained in MOF pores. By washing the porous material with an appropriate solvent, the new solvent molecules replace whatever molecules had remained in the pores and are subsequently removed by a gentle evaporation process. The solvent used for extraction can be identical to or different from that used for the reaction of the at least one metal ion with the at least one organic ligand which is at least bidentate. As non-limiting suitable solvents for the purification or extraction step the following can be mentioned: water, methanol, ethanol, isopropanol, heptane, hexane, pentane, cyclohexane, alkenes, DMF, DEF, DMSO, dioxane, chloroform, dichloromethane, diethyl ether, acetonitrile, toluene, benzene, THF, chlorobenzene, ethylene glycol, and mixtures thereof.

Any MOF can be obtained by the process of the invention. In a preferred embodiment, the dry crystalline MOF obtained by this method is selected from the group consisting of Cu-benzene-1,3,5-tricarboxylic acid, Zn-2,5-dihydroxy-1,4-benzenedicarboxylic acid, Cu-biphenyl-3,3',5,5'-tetracarboxylic acid, Fe-(E)-butenedioic acid, Zn-benzene-1,4-dicarboxylic acid, Zn-imidazole, Zn-2-methyl-1H-imidazole, Zn-4-methyl-5-imidazolecarboxaldehyde, Fe-2-amino-1,4-benzenedicarboxylic acid, Co-adenine-acetic acid, Zn-adenine-biphenyl-4,4'-dicarboxylic acid, Ni-aspartic acid, Ni-aspartic acid-4,4-bipyridine, Zn-aspartic acid, Cu-biphenyl-3,4',5-tricarboxylic acid, Zn-biphenyl-4,4'-dicarboxylic acid, Zn-1,3,5-tris(4-carboxyphenyl)benzene, Zn-1,4-naphthalenedicarboxylic acid, Zn-naphthalene-2,6-dicarboxylate, Zn-pyrene-2,7-dicarboxylic acid, or Zn-4,5,9,10-tetrahydropyrene-2,7-dicarboxylic acid, Zn-1,4-naphthalenedicarboxate, or Zn-naphthalene-2,6-dicarboxylate-diazabicyclo [2.2.2]octane.

As mentioned above, the dry MOF crystals obtained by the present process often have particularly small dimensions. In one embodiment the MOF crystals have a size ranging between 0.01 and 100 μm. In another embodiment, the size of the obtained MOF crystals is between 0.01 to 1 μm. Additionally, the present process can yield MOF crystals in the form of spherical microcapsules, which are maintained after the purification step. Such MOF capsules can be obtained by employing low reactant concentrations. Thus, in a particular embodiment the obtained crystalline MOF product is in the form of spherical microcapsules. The microcapsules obtained by the present process are constituted by MOF crystals of small size, for example a size ranging between 0.01 and 10 μm.

The MOF material obtained by the present process can be used as such or it can be transformed into a shaped body. In shaped body production, the MOF can be mixed with further materials, such as, for example, binders, lubricants or other additives, which are added during the production. Likewise, the shaped body may comprise further components such as, for example, adsorbents, such as activated carbon. For the production of these shaped bodies, in principle all suitable methods are possible. Non-limiting methods for producing shaped bodies are:

a) Kneading/pan-grinding the framework material alone or together with at least one binder and/or at least one pasting agent and/or at least one template compound to obtain a mixture; shaping the resultant mixture by means of at least one suitable method such as, for example, extrusion; optionally washing and/or drying and/or calcining the extrudate; and optionally final processing.

b) Tableting or pelleting together with at least one binder and/or other aid.

c) Applying the framework material to at least one porous support material if appropriate. The resultant material can then be further processed in accordance with the above-described method to give a shaped body.

The MOFs obtained by the process of the invention, and/or the shaped bodies obtained thereof, can be used for any use in which a highly porous material is needed. Typical uses for MOFs are taking up of at least one substance for its storage, ion-exchange, sensor and separation of substances. Preferably, the at least one substance is a gas, still more preferably, the gas is hydrogen and carbon dioxide. The obtained MOFs and/or the shaped bodies obtained thereof can also be used for encapsulation and controlled release of chemical substances and catalysis. Further, the obtained MOFs and/or the shaped bodies obtained thereof can be used for drug delivery and as contrast agents.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

The following examples are provided by way of illustration, and are not intended to be limiting of the present invention.

Example 1

Production of a Cu-benzene-1,3,5-tricarboxylic acid (Cu-1,3,5-BTC) MOF 2.05 g of $Cu(NO_3)_2 \cdot 2.5H_2O$ (Sigma-Aldrich) in 25 ml of a mixture of dimethylformamide (DMF, Romil), ethanol (Romil) and water ($V_{DMF}:V_{ethanol}:V_{water}$—1:1:1) was added to a solution of 1.17 g of benzene-1,3,5-tricarboxylic acid (1,3,5-BTC, Sigma-Aldrich) in 25 ml of a mixture of DMF, ethanol and water ($V_{DMF}:V_{ethanol}:V_{water}$—1:1:1). The resulting mixture was spray-dried on the Mini Spray Dryer B-290 (BÜCHI labortechnik AG, Flawil, Switzerland) using a two-fluid nozzle at a feed flow of 4.5 ml/min, gas spray flow of 26.25 $m^3/h$, inlet air temperature of 180° C., outlet air temperature of 120° C., and with a spray cap with 0.5 mm-hole-size. After 11 minutes a dry blue powder was obtained.

The dry product (submicron crystals with sizes 150±50 nm) was subsequently washed with 3×60 ml of methanol and dried in vacuum for 12 h at 120° C.

The yield was 1.45 g (75% w/w). The specific surface area of the MOF (BET method) was 1144 $m^2/g$.

Figure 1:
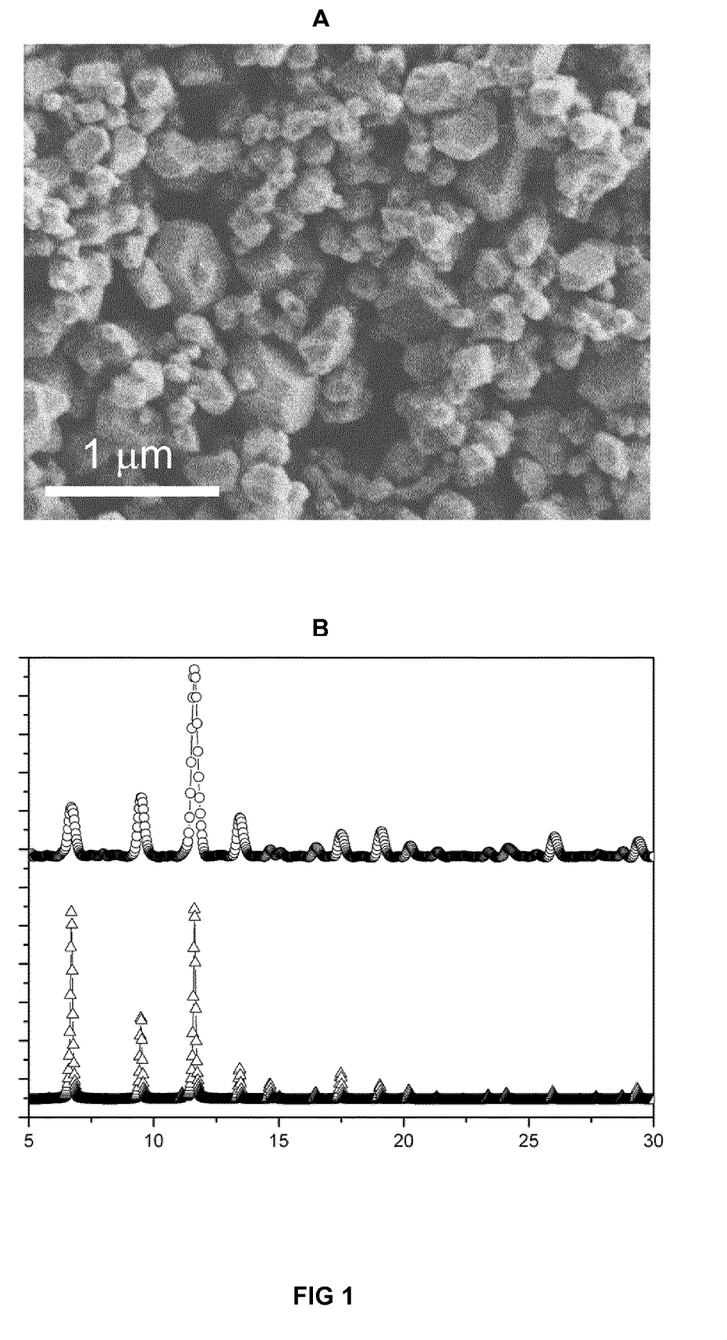
FIG. 1. (A) Scanning electron microscopy (SEM) image of Cu-1,3,5-BTC MOF submicron crystals. (B) X-ray powder diffraction (XRPD) pattern of Cu-1,3,5-BTC MOF crystals (top), compared with the simulated XRPD of Cu-1,3,5-BTC MOF (also known as HKUST-1, bottom). X axis represents Angle $2\theta$ (°).

FIG. 1 shows the scanning electron microscopy (SEM) image of the obtained crystals and their X-ray powder diffraction (XRPD) pattern compared with the simulated XRPD of Cu-1,3,5-BTC MOF (also known as HKUST-1) reported in the literature (Chui S. S. Y., Samuel L. M. F., Chamant J. P. M., Orpen A. J, Williams I. D. "A chemically functionalizable nanoporous material $[Cu_3(TMA)_2(H_2O)_3]_n$,", *Science* 1999, vol. 283, p. 1148-1150). It can be observed that the XRPD patters are the same, thus demonstrating that the process of the invention was able to produce the same MOF.

Example 2

Production of a Cu-1,3,5-BTC MOF 2.05 g of $Cu(NO_3)_2.2.5H_2O$ (Sigma-Aldrich) in 25 ml of a mixture of DMF (Romil), ethanol (Romil) and water ($V_{DMF}:V_{ethanol}:V_{water}$—1:1:1) were added to a solution of 1.17 g of 1,3,5-BTC (Sigma-Aldrich) in 25 ml of a mixture of DMF, ethanol and water ($V_{DMF}:V_{ethanol}:V_{water}$—1:1:1). The resulting mixture was spray-dried on the Nano Spray Dryer B-90 (BÜCHI labortechnik AG, Flawil, Switzerland) at a feed flow of 2 ml/min, gas spray flow of 26.25 $m^3/h$, inlet air temperature of 120° C., outlet air temperature of 100° C., and with a spray cap with 7 μm-hole-size. After 12 minutes a dry blue powder was collected.

The powder (submicron crystals with sizes 150±20 nm) was then washed with 3×60 ml of methanol and dried in vacuum for 12 h at 120° C.

The yield was 1.56 g (85% w/w). The specific surface area (BET method) was 1266 $m^2/g$.

Example 3

Production of Cu-1,3,5-BTC MOF Capsules

A solution of 0.317 g of $Cu(NO_3)_2.2.5H_2O$ (Sigma-Aldrich) in 400 ml of a mixture of DMF (Romil), ethanol (Romil) and water ($V_{DMF}:V_{ethanol}:V_{water}$—1:1:1) were added to a solution of 0.185 g of 1,3,5-BTC (Sigma-Aldrich) in 400 ml of a mixture of DMF, ethanol and water ($V_{DMF}:V_{ethanol}:V_{water}$—1:1:1). The resulting mixture was spray-dried on the Mini Spray Dryer B-290 (BÜCHI labortechnik AG, Flawil, Switzerland) using a two-fluid nozzle at a feed flow of 4.5 ml/min, gas spray flow of 26.25 $m^3/h$, inlet air temperature of 180° C., outlet air temperature of 120° C., and with a spray cap with 0.5 mm-hole-size. After 3 hours a blue powder comprised of microcapsules was obtained. The microcapsules were washed with 2×10 ml of methanol and 10 ml of $CH_2Cl_2$. The final product (capsules with sizes 2.5 μm±0.4 μm) was dried in vacuum for 12 h at 120° C.

The yield was 0.20 g (70% w/w). The specific surface area (BET method) was 1209 $m^2/g$.

Figure 2:
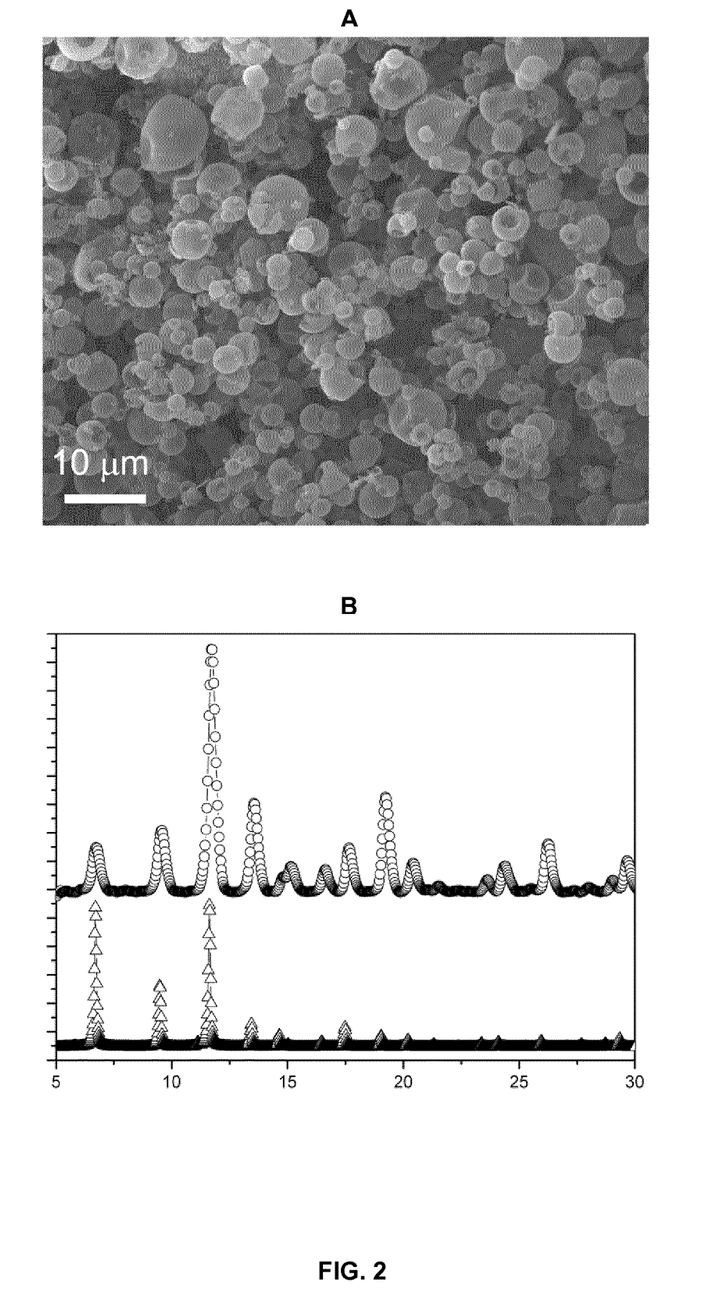
FIG. 2. (A) SEM image of Cu-1,3,5-BTC MOF capsules. (B) XRPD pattern of Cu-1,3,5-BTC MOF capsules (top), compared with the simulated XRPD of Cu-1,3,5-BTC (also known as HKUST-1, bottom). X axis represents Angle $2\theta$ (°).

FIG. 2 shows the scanning electron microscopy image of the obtained capsules. Their X-ray powder diffraction (XRPD) pattern compared with the simulated XRPD of Cu-1,3,5-BTC MOF (also known as HKUST-1) reported in the literature (Chui S. S. Y., et al, supra) is also shown.

Example 4

Preparation of a Zn-2,5-dihydroxy-1,4-benzenedicarboxylic acid (DHTA) MOF 2.58 g of $Zn(NO_3)_2.6H_2O$ (Sigma-Aldrich) in 25 ml of DMF (Romil) was added to a solution of DHTA (Sigma-Aldrich) in 25 ml of DMF. 2.5 ml of water were then added to this mixture. The resulting mixture was spray-dried on the Mini Spray Dryer B-290 (BÜCHI labortechnik AG, Flawil, Switzerland) using a two-fluid nozzle at a feed flow of 4.5 ml/min, gas spray flow of 26.25 $m^3/h$, inlet air temperature of 180° C., outlet air temperature of 120° C., and with a spray cap with 0.5 mm-hole-size. After 11 minutes a brown powder was obtained. The brown powder was washed with 3×60 ml of methanol (Romil). The product (submicron crystals with sizes 100±10 nm) was dried in vacuum for 10 h at 150° C. and 12 h more at 265° C.

The yield was 0.40 g (40% w/w).

Figure 3:
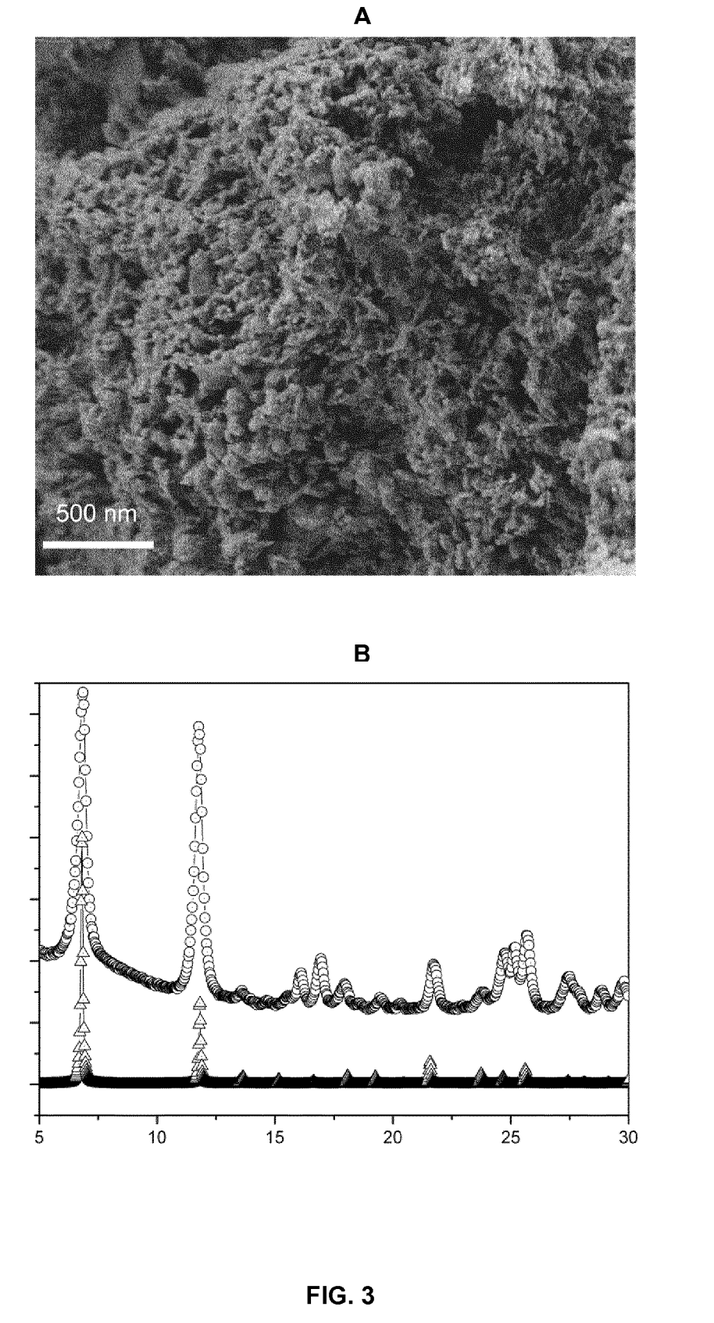
FIG. 3. (A) SEM image of Zn-DHTA MOF submicron crystals. (B) XRPD pattern of Zn-DHTA MOF crystals (top), compared with the simulated XRPD of Zn-DHTA (also known as MOF-74, bottom). X axis represents Angle $2\theta$ (°).

The X-ray powder diffraction (XRPD) pattern of the obtained MOF and the simulated XRPD of Zn-DHTA MOF (also known as MOF-74) reported by Rosi et al (Rosi N. L., Kim J., Eddaoudi M., Chen B., O'Keeffe M., Yaghi O. M. "Rod packings and metal-organic frameworks constructed from rod-shaped secondary building units", *Journal of the American Chemical Society* 2005, vol. 127, p. 1504-1518) demonstrate that the MOF produced by the present process is identical to that described in the literature.

Example 5

Preparation of a Cu-biphenyl-3,3',5,5'-tetracarboxylic acid MOF 0.22 g of $Cu(NO_3)_2.2.5H_2O$ (Sigma-Aldrich) in 25 ml of DMF (Romil) were added to a solution of 0.16 g of biphenyl-3,3',5,5'-tetracarboxylic acid (Sigma-Aldrich) in 32 ml of DMF. 17 ml of water was then added to this mixture. The resulting mixture was spray-dried on the Mini Spray Dryer B-290 (BÜCHI labortechnik AG, Flawil, Switzerland) using a two-fluid nozzle at a feed flow of 4.5 ml/min, gas spray flow of 26.25 $m^3/h$, inlet air temperature of 180° C., outlet air temperature of 120° C., and with a spray cap with 0.5 mm-hole-size. After 15 minutes a bluish powder was obtained. The bluish powder was washed with 3×60 ml of methanol (Romil). The product (nanocrystals with sizes of 50±10 nm) was dried in vacuum for 10 h at 120° C.

The yield was 0.25 g (70% w/w). The specific surface area (BET method) was 1140 $m^2/g$.

Figure 4:
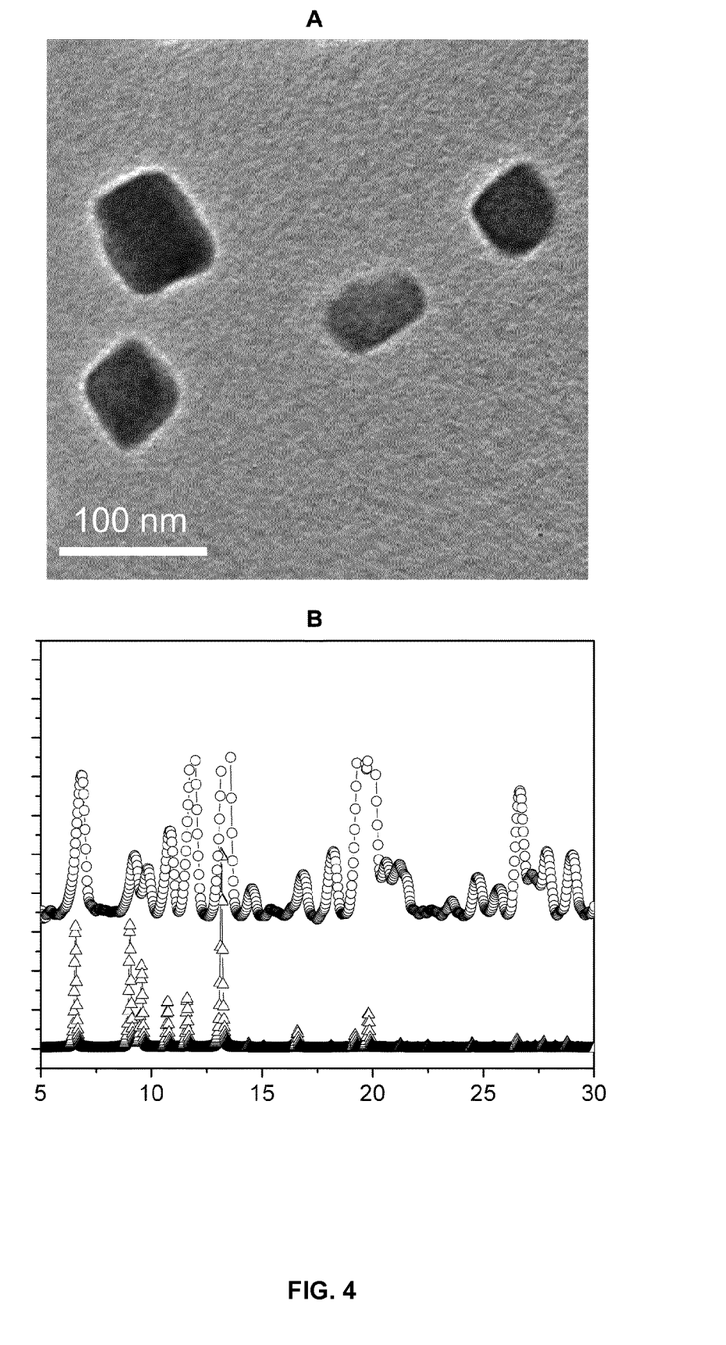
FIG. 4. (A) Transmission electron microscopy (TEM) image of Cu-biphenyl-3,3',5,5'-tetracarboxylic acid MOF nanocrystals. (B) XRPD pattern of Cu-biphenyl-3,3',5,5'-tetracarboxylic acid MOF crystals (top), compared with the simulated XRPD of Cu-biphenyl-3,3',5,5'-tetracarboxylic acid (also known as NOTT-100 or MOF-505, bottom). X axis represents Angle $2\theta$ (°).

FIG. 4 shows the transmission electron microscopy (TEM) image of the obtained crystals and their X-ray powder diffraction (XRPD) pattern compared with the simulated XRPD of Cu-biphenyl-3,3',5,5'-tetracarboxylic acid (also known as NOTT-100 or MOF-505) reported in the literature (Chen B., Ockwig N. W., Millward A. R., Contreras D. S., Yaghi O. M. "High $H_2$ adsorption in a microporous metal-organic framework with open metal sites", *Angewandte Chemie Interna-*

Example 6

Preparation of Fe-(E)-butenedionic acid MOF

A solution of 0.28 g of $FeCl_3 \cdot 6H_2O$ (Sigma-Aldrich) in 5 ml of water and a solution of 0.12 g of (E)-butenedionic acid (Sigma-Aldrich) in 5 ml of water were prepared. 1 ml of 2 M aqueous NaOH solution was added to the (E)-butenedionic acid solution. Both solutions were simultaneously spray-dried on the Mini Spray Dryer B-290 (BÜCHI labortechnik AG, Flawil, Switzerland) using a three-fluid nozzle at a feed flow of 4.5 ml/min, gas spray flow of 26.25 m³/h, inlet air temperature of 180° C., and outlet air temperature of 120° C. After 5 minutes a brown powder was obtained. The powder was washed with 30 ml of DMF (Romil) followed by 30 ml of water. The final product (submicron crystals with sizes of 100±20 nm) was then dried in vacuum for 10 h at 120° C.

The yield was 0.25 g (70% w/w).

Figure 5:
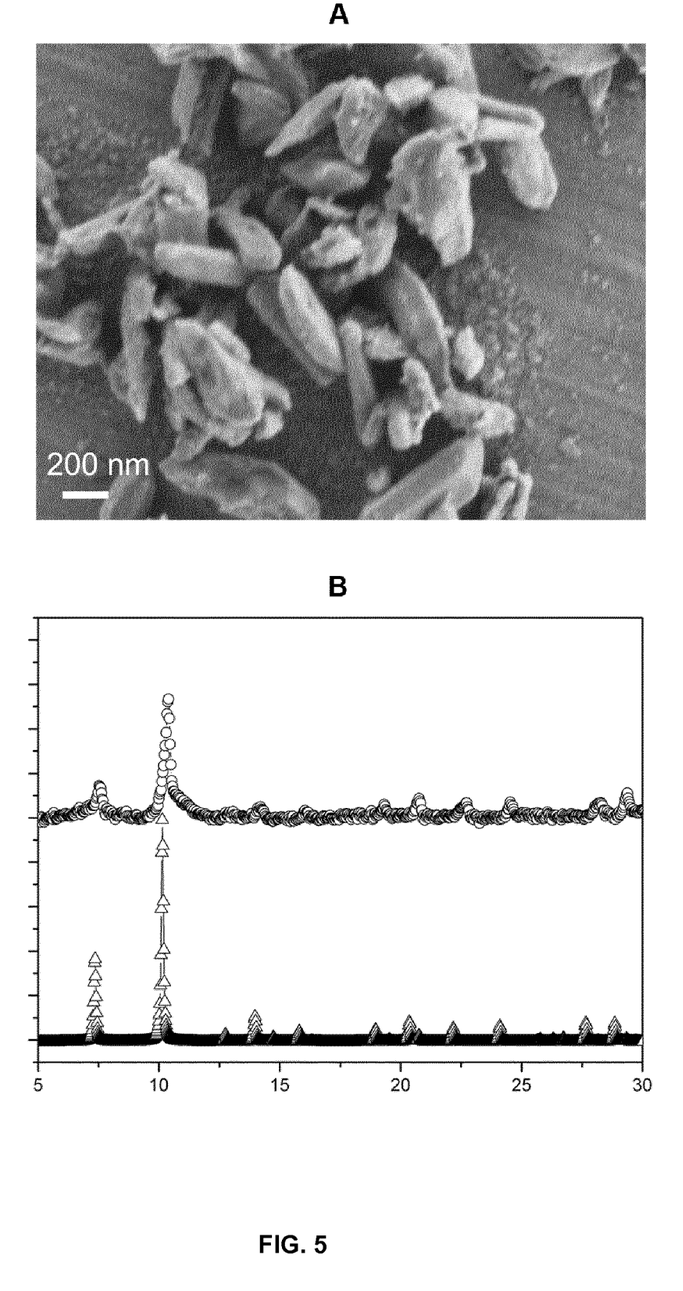
FIG. 5. (A) SEM image of Fe-(E)-butenedionic acid MOF submicron crystals. (B) XRPD pattern of Fe-(E)-butenedionic acid MOF crystals (top), compared with the simulated XRPD of Fe-(E)-butenedionic acid (also known as MIL-88A, bottom). X axis represents Angle $2\theta$ (°).

FIG. 5 shows the scanning electron microscopy (SEM) image of the obtained crystals and their X-ray powder diffraction (XRPD) pattern compared with the simulated XRPD of Fe-(E)-butenedionic acid (also known as MIL-88A) reported in the literature (Chalati T., Horcajada P., Gref R., Couvreur P., Serre C. "Optimization of the synthesis of MOF nanoparticles made of flexible porous iron fumarate MIL-88A", *Journal of Materials Chemistry* 2011, vol. 21, p. 2220-2227). The patterns are identical, which demonstrates that the present process produced the same MOF.

The invention claimed is:

1. A process for the preparation of a dry crystalline metal organic framework which comprises:
   a) spray drying at least one metal ion and at least one organic ligand which is at least bidentate into a spray dryer in the presence of a solvent, wherein the reaction of the at least one metal ion with the at least one organic ligand to yield the metal organic framework and the drying of the obtained metal organic framework take place simultaneously inside the spray dryer, and
   b) collecting the formed dry crystalline metal organic framework.

2. The process according to claim 1, wherein the at least one metal ion is selected from the group consisting of Zn, Cu, Ni, Co, Fe, Mn, Cr, Cd, Mg, Ca, Zr, Gd, Eu, Tb, and mixtures thereof.

3. The process according to claim 1, wherein the at least one organic ligand which is at least bidentate contains at least one functional group selected from the group consisting of a carboxylate, a phosphonate, an amine, an azide, a cyanide, a squaryl, a heteroatom, and mixtures thereof.

4. The process according to claim 3, wherein the at least one organic ligand which is at least bidentate is a monocarboxylic acid, a dicarboxylic acid, a tricarboxylic acid, a tetracarboxylic acid, imidazole, or mixtures thereof.

5. The process according to claim 4, wherein the at least one organic ligand which is at least bidentate is selected from the group consisting of formic acid, acetic acid, oxalic acid, propanoic acid, butanedioic acid, (E)-butenedioic acid, benzene-1,4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E,4E)-hexa-2,4-dienedioic acid, 1,4-naphthalenedicarboxylic acid, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, pyridine-4-carboxylic acid, pyridine-3-carboxylic acid, imidazole, 1H-benzimidazole, 2-methyl-1H-imidazole, and mixtures thereof.

6. The process according to claim 1, wherein the solvent is selected from the group consisting of water, methanol, ethanol, isopropanol, N,N-dimethyl formamide, N,N-diethyl formamide, dimethyl sulfoxide dioxane, chloroform, dichloromethane, diethyl ether, acetonitrile, toluene, benzene, tetrahydrofuran, chlorobenzene, ethylene glycol, hexane, pentane, and mixtures thereof.

7. The process according to claim 1, wherein a liquid solution containing both the at least one metal ion and the at least one organic ligand which is at least bidentate is sprayed into the spray dryer.

8. The process according to claim 1, wherein the reaction takes place when two liquid solutions, one containing the at least one metal ion and another containing the at least one organic ligand which is at least bidentate, are simultaneously sprayed into the spray dryer.

9. The process according to claim 1, wherein the reaction takes place in the presence of a base.

10. The process according to claim 9, wherein the base is selected from the group consisting of metal alkaline or earth alkaline hydroxides, amines, metal alkaline or earth alkaline carbonates, metal alkaline or earth alkaline acetates, pyridines, azoles, diazines, and mixtures thereof.

11. The process according to claim 1, wherein the reaction temperature is between 80 and 200° C.

12. The process according to claim 1, further comprising a purification step which comprises washing the crystalline metal organic framework with an appropriate solvent, followed by drying the obtained crystalline metal organic framework.

13. The process according to claim 1, where the obtained dry crystalline metal organic framework is Cu-benzene-1,3,5-tricarboxylic acid, Zn-2,5-dihydroxy-1,4-benzenedicarboxylic acid, Cu-biphenyl-3,3',5,5'-tetracarboxylic acid, Fe-(E)-butenedioic acid, Zn-benzene-1,4-dicarboxylic acid, Zn-imidazole, Zn-2-methyl-1H-imidazole or Fe-2-amino-1,4-benzenedicarboxylic acid.

14. The process according to claim 1, which is a continuous process.

* * * * *